United States Patent [19]
Sabin

[11] Patent Number: 5,873,368
[45] Date of Patent: Feb. 23, 1999

[54] TRANSCUTANEOUS DEVICE AND METHOD FOR ELECTRICAL CONNECTIONS THROUGH THE SKIN

[75] Inventor: Pierre Sabin, 696 rue Robert Pinchon, 76230 Bois Guillaume, France

[73] Assignees: Pierre Sabin, Guillaume; Jean Louis Sabin, Sainte Luce; Jean-Marie Hugueny, Regnie-Durette; Antoine Warnier, Paris, all of France

[21] Appl. No.: 875,092
[22] PCT Filed: Jan. 26, 1996
[86] PCT No.: PCT/FR96/00141
  § 371 Date: Jul. 22, 1997
  § 102(e) Date: Jul. 22, 1997
[87] PCT Pub. No.: WO96/22727
  PCT Pub. Date: Aug. 1, 1996

[30] Foreign Application Priority Data

Jan. 26, 1995 [FR] France ................................. 95/00882

[51] Int. Cl.$^6$ ..................................................... A61B 19/00
[52] U.S. Cl. ............................................................. 128/899
[58] Field of Search ............................. 128/899; 600/373, 600/383, 544; 607/52, 57

[56] References Cited

U.S. PATENT DOCUMENTS 3,765,032  10/1973  Palma ....................................... 128/899
5,507,303   4/1996  Kuzma ..................................... 128/899

Primary Examiner—William E. Kamm
Attorney, Agent, or Firm—Young & Thompson

[57] ABSTRACT

A transcutaneous device includes a base for attachment to a bone. The device includes a temporary stopper and a transcutaneous pillar containing electrical connections complementary to the electrical connections incorporated in the base. The base also comprises a sealed bacteriological protective membrane which can be perforated by electrically conductive pins of the electrical connections.

14 Claims, 5 Drawing Sheets

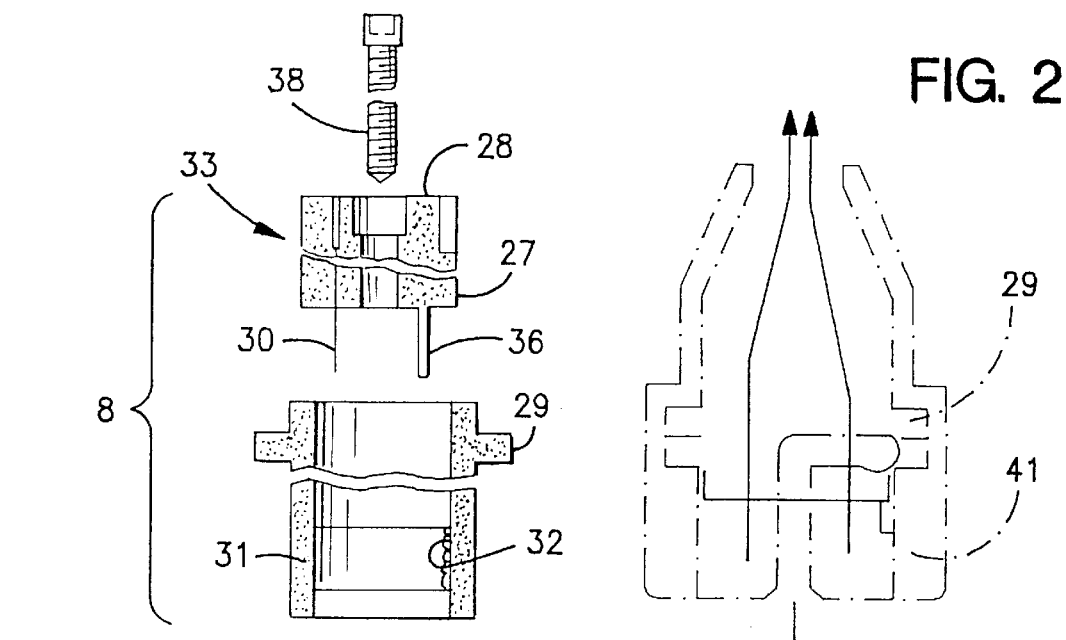
FIG. 2
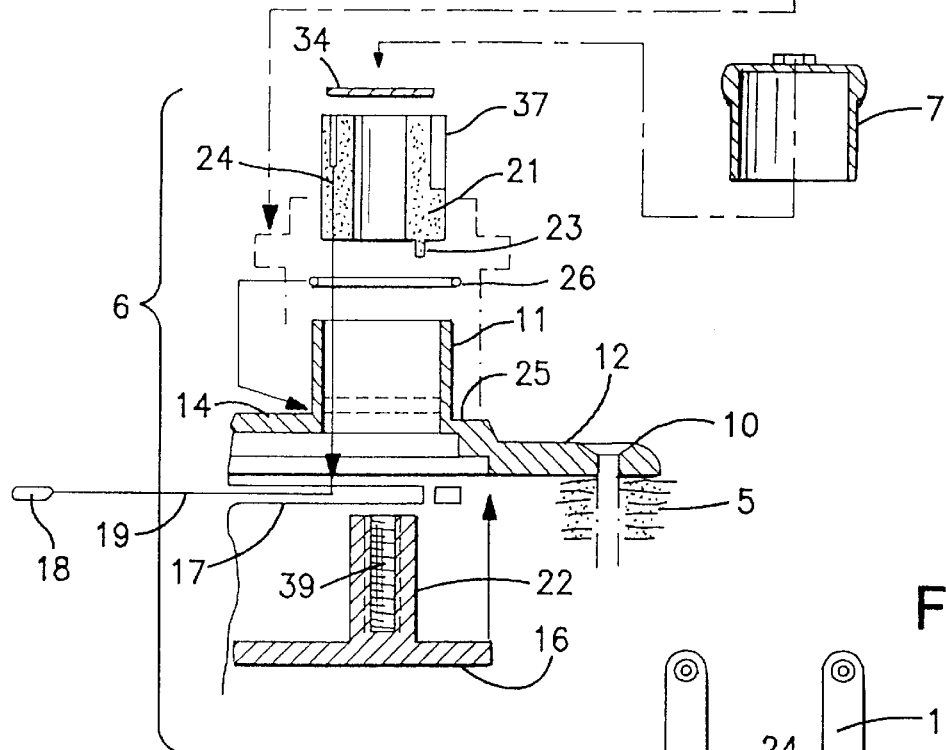
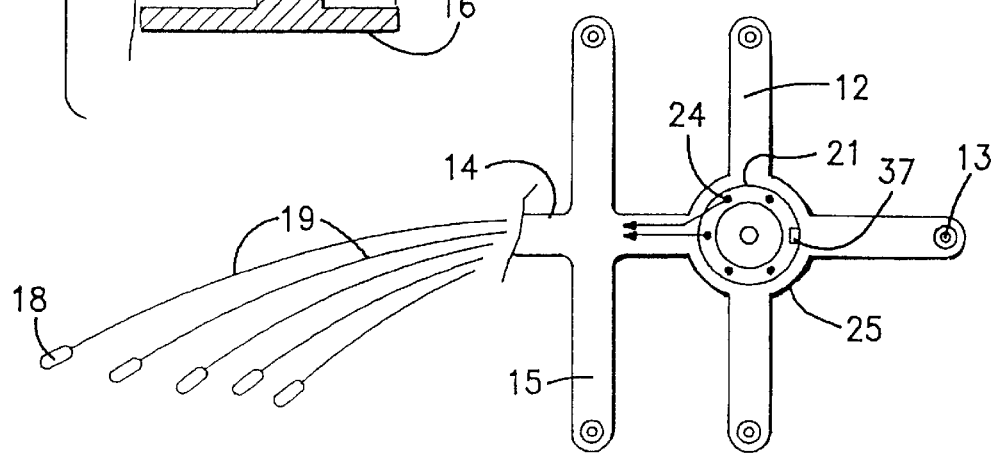
FIG. 3

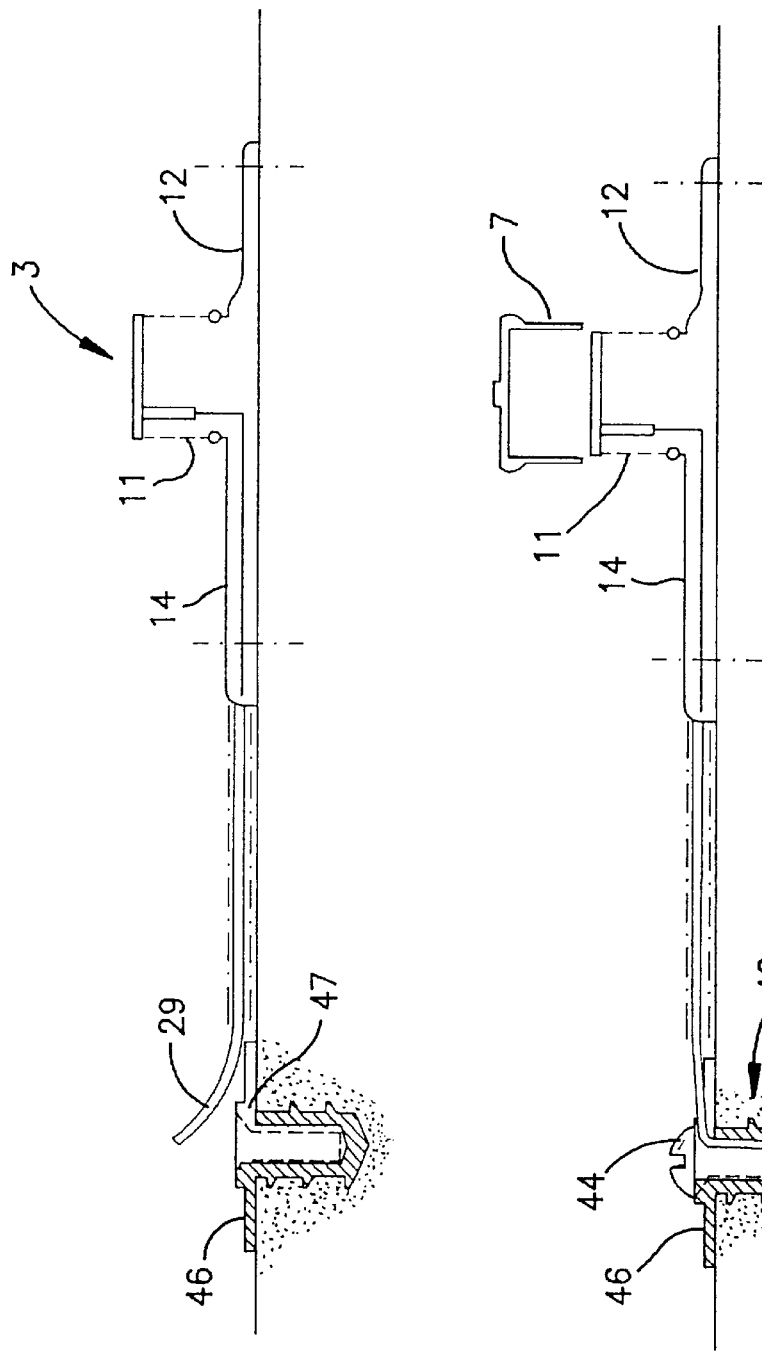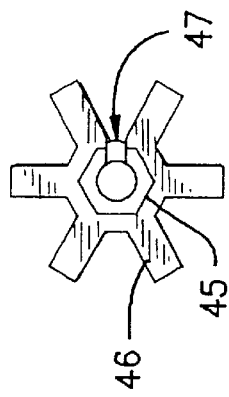

TRANSCUTANEOUS DEVICE AND METHOD FOR ELECTRICAL CONNECTIONS THROUGH THE SKIN

The present invention relates to medical equipment. Its subject is a device or item of equipment which, according to at least its preferred embodiments, is applicable for the diagnosis, prevention and/or treatment of various dysfunctions which can be observed in the animal or human body.

The invention essentially relates to enabling the body to be equipped with an implanted transcutaneous device designed to make electrical connections through the skin. With such a device, electrical signals may be transmitted through the skin, from sensors permanently implanted in the body, in order to be used by external items of equipment for processing the information carried by these signals. The information from the sensors is thus made available without suffering the losses arising from the connective tissues which the signals have to pass through in the case of external sensors placed on the skin, even if only the epidermis. It is also possible to transmit, from the outside, an electric supply current for an electromechanical apparatus implanted inside the human body, in particular to recharge a cell and/or battery which the patient is able to keep permanently without having to undergo an operation in order to change it periodically.

To do this, the invention provides a medical equipment device and method for making electrical connection through the skin. The device comprises a transcutaneous device which includes a socket provided with means for fixing it to a bone in the body and means for making a sealed connection alternately to a temporary plug and a transcutaneous stud inside which there is a male connector for electrical connection, complementary to a female connector for electrical connection incorporated in the said socket, and in that the said socket includes an impermeable membrane for the bacteriological protection of the said female connector, which membrane can be perforated by at least electrically conducting pins which form part of the said electrical connection means.

By virtue of this design, the transcutaneous connection device of the invention is easy to put into place, while preserving the quality of the electrical contact between male connector and female connector. During a first surgical operation, the socket is fixed to a bone, the socket as received from the factory being equipped with its bacteriological protective membrane and with its temporary plug, which in particular provides sealing against blood. After a sufficient time to allow stabilization of the socket by osteointegration, the bacteriological protective membrane provides sealing during the second installation step during which the temporary plug is replaced by the transcutaneous stud which arrives from the factory equipped with its male connector. This stud is permanently fastened to the socket, for example using an axial screw, in the position providing the sealed connection and the electrical connections between connectors by the perforation of the membrane.

Moreover, it will be understood from the following description that, according to the embodiments and the modes of implementation of the invention which are tailored to each particular application, the various functions of the essential components of the invention may be provided by equivalent means, often even preferred means in the light of the requirements of industrial practice.

In particular, it will be seen below that the notions of female connector and male connector are not limiting and that they do not always necessarily imply a physical action of the mechanical penetration of a so-called male pin or connector into a so-called female pin or connector. It will also be seen below that, depending on the embodiments to be applied preferably in conjunction with the particular practical applications, the components providing the electrical connections according to the invention may be provided, in every case partly, either on the socket implanted during the first surgical operation, or within the stud put into place during the second surgical operation, or alternatively in a removable connector which temporarily replaces, between two series of medical tests, a cap which closes off the transcutaneous stud when not in use, providing connection to the other components of the device according to the invention which are permanently implanted in the body.

According to some of the preferred embodiments of the invention, the electrical connection means may be permanently fixed partly in the socket subcutaneously implanted in the body, partly in the stud, put into place during a second surgical operation, for permanent access from the outside, and/or partly in an interacting connector fulfilling an intrinsic role in the electrical connections through the stud.

The medical equipment system comprising an implant according to the invention exhibits, inter alia, technological features associated with the specific construction of the electrical connections, such as will be more specifically described and claimed hereinbelow. In particular, it should be noted that the notions of male connectors and female connectors do not necessarily imply penetration of one into the other and that components according to the invention fulfilling their respective functions may be integrated into or associated with various essential components of the equipment of the invention, depending on the choices which take into consideration industrial practice.

One particular embodiment of the invention which will make the essential characteristics and advantages more clearly understood will now be described in more detail, with various alternative forms, it being understood, however, that this embodiment is chosen by way of example and that it is in no way limiting.

Its description is illustrated by FIGS. 1 to 6 of the appended drawings, in which:

FIG. 2 shows the various constituent components of the transcutaneous implanted device of the equipment of the invention, in exploded view and in longitudinal section;

FIG. 3 shows a diagrammatic view, from above, of the socket forming part of this device;

FIG. 4 shows diagrammatically the same socket of the transcutaneous device in its connection to a subcutaneous implant;

Figure 7:
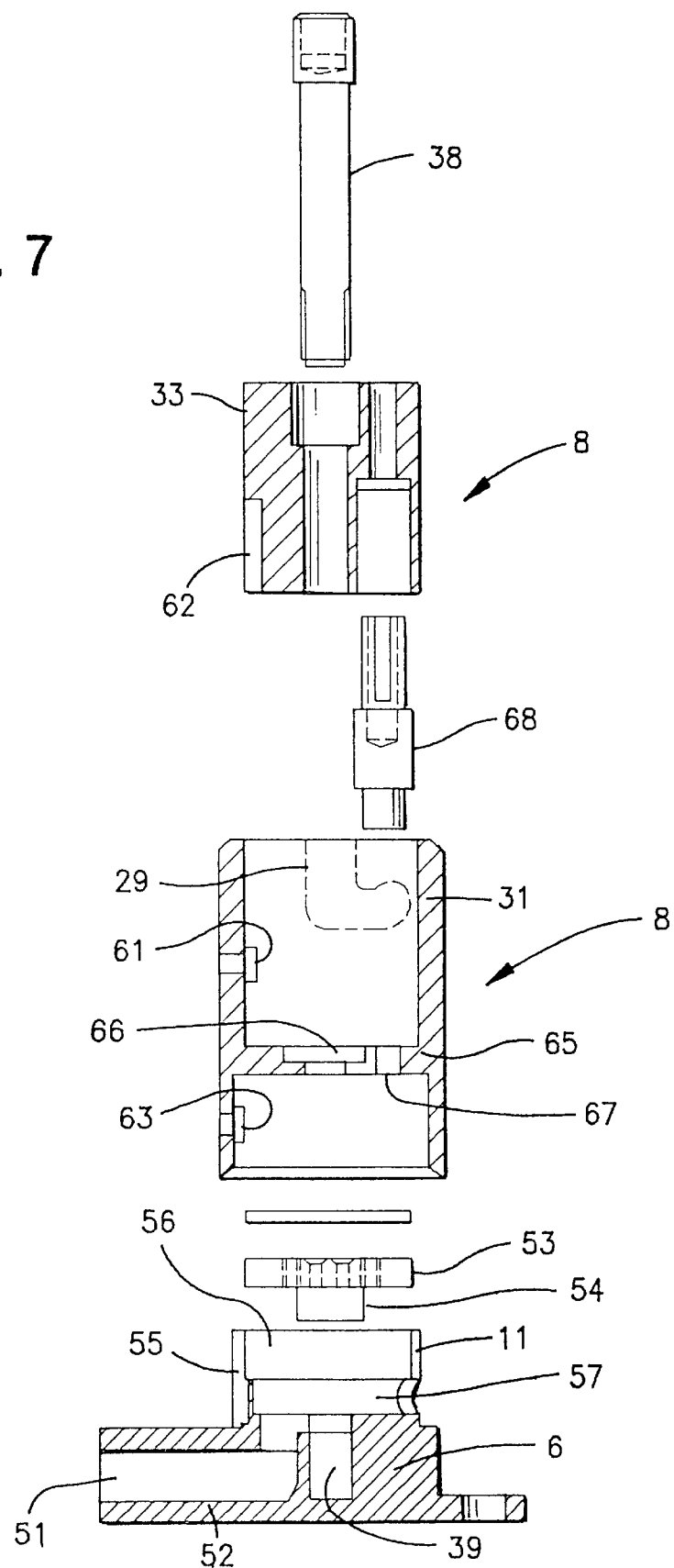
Figure 10:
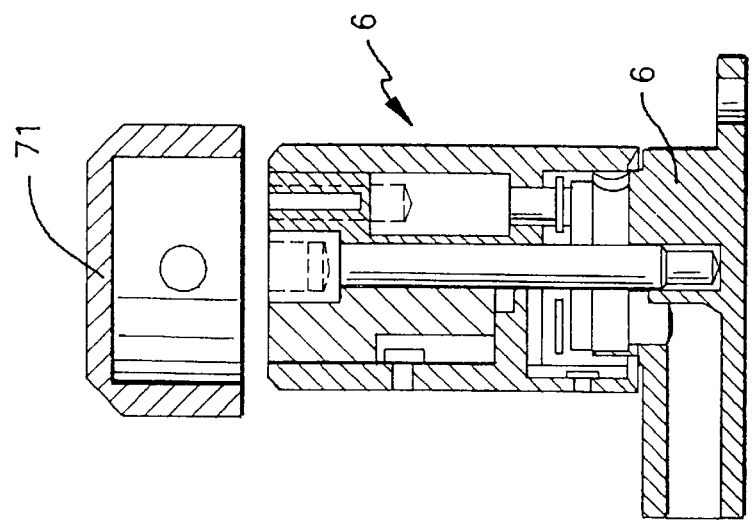
Figure 9:
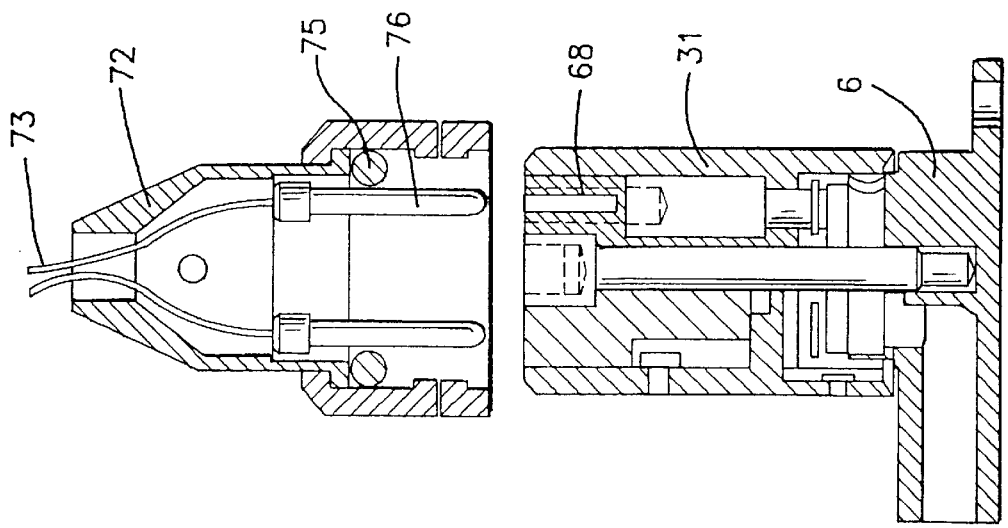
Figure 8:
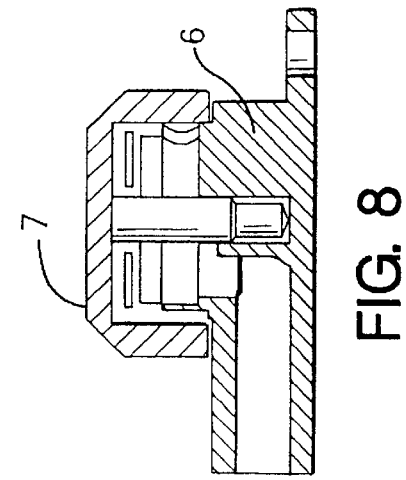

FIG. 5 corresponds to FIG. 4 with the subcutaneous implant completed;

FIG. 6 is a partial view, from above, of such a subcutaneous implant;

FIG. 7 illustrates, in an exploded view, a second embodiment of the invention;

FIG. 8 shows, in longitudinal section, the device of FIG. 7 in the first stage of the implantation operations;

FIG. 9 shows the device of FIGS. 7 and 8, illustrating its connection to a connector for electrical connection outside the body;

FIG. 10 illustrates, likewise, the device when the individual wearing it is not under observation, the connector 72 in FIG. 9 then being replaced by a protective cap 71.

For reasons of clarity, the same components have been labelled by the same references and the representation of the drawings is diagrammatic.

In a particular embodiment described, which constitutes one particularly advantageous form of implementation of the invention, the medical equipment, forming the subject of the invention, is designed to capture information permanently transmitted by an electric current from an organ in the human body, such as the cranium in respect of an electroencephalogram or the myocardium in respect of an electrocardiogram, from receivers implanted in the body. However, it can also be used, simultaneously or separately, to supply an electric current or control a similarly implanted receiver, as may be the case with a pacemaker or any other electromechanical device.

Figure 1:
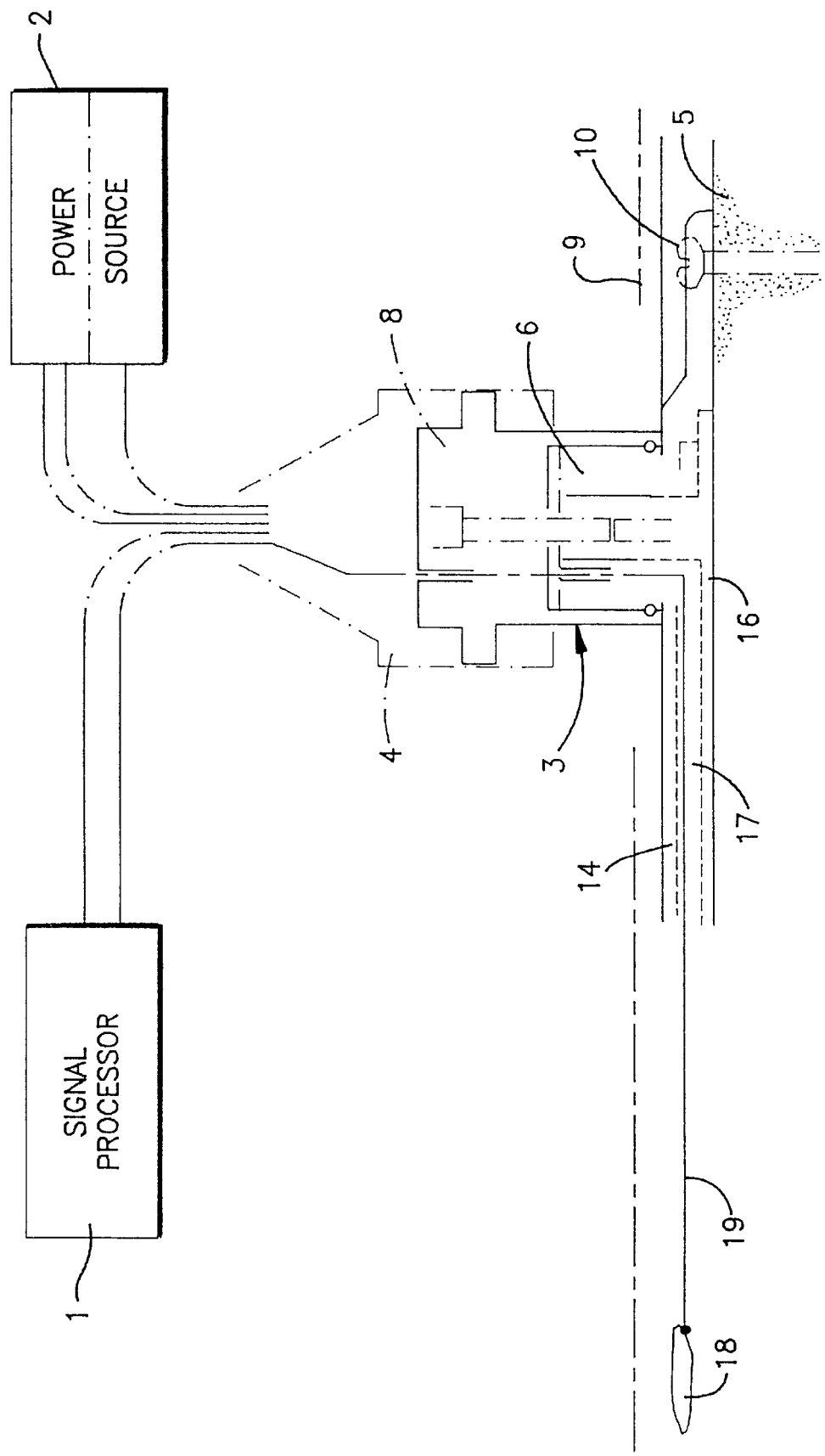
FIG. 1 shows an overall diagram of a device according to the invention associated with signal-processing units.

This is why FIG. 1 shows items of equipment external to the body, namely in particular a unit 1 for processing electrical signals coming from suitable sensors in the body, which pick up these signals and transmit them to the unit 1 through the transcutaneous device of the invention, and a unit 2 for supplying or recharging a cell or battery also implanted in the body in question. All the electrical connections necessary for operating such items of equipment are provided through an associated transcutaneous device 3 (or a juxta-osseous implant), produced according to the invention, by means of an external intermediate connector 4 which is removable.

The transcutaneous device 3 is put into place, according to the invention, by an implementation method which comprises two surgical steps. The first step consists in permanently fixing, to a bone 5 in the body relatively close to the skin, a socket 6, forming part of the device of the invention, which is, however, closed by a temporary plug 7 (FIG. 2). During the second step, once the socket has been stabilized by osteointegration, the temporary plug 7 is replaced by a transcutaneous stud 8. It is to the latter that the units 1 and 2 will be connected, at opportune times, via the removable external connector 4, in order thereby to be electrically connected through the skin to the sensors and other items of equipment permanently implanted inside the body.

The temporary plug 7, like the stud 8, is produced in various models, which are advantageously interchangeable on the same socket 6, so that the system can be easily adapted to various lengths depending on the depth of the implantation bone with respect to the skin and to the thickness of biological tissue which has thereby to be penetrated. From this point of view, and especially for an application involving periodic electroencephalograms, it will be particularly appreciated to be able to fix the transcutaneous device to the cranium, just behind the ear, so that the visible part is concealed by the auricle.

The socket 6, seen from above as shown in FIG. 3, forms, around a central shank 11, radial fixing flanges 12, which have at their end a hole 13 in which the countersunk head of a screw 10 for fixing to the bone is placed (FIGS. 1 and 2), and also a radial arm 14 which also has two similar fixing flanges 15. The flanges 12 and 15 and the arm 14 constitute the socket's base which is made either, preferably, of pure titanium as a single piece with the shank 11, or made of another biocompatible material, such as silicone-based organic resins. The shank 11 has, for example, a diameter of about 6 mm.

Under this base, on the opposite side of the shank 11, is fitted a baseplate 16, also made of titanium, which is factory-welded to the base of the socket and which engages in the base in order to lock in a support plate 17 along the entire length of the arm 14.

The support plate 17 constitutes the support for longitudinal electrical conductors which are made in the form of printed circuits. Each of the various conductors, which will, for example, be 5, 7 or 9 in number, terminates on the upper face of the support plate 17 inside the shank 11, while, at its other end, an autonomous conducting wire is soldered to it, which autonomous conducting wire will be, in particular, a gold wire sheathed with a biocompatible material such as a silicone resin. The various conducting wires 19 thus leave the end of the arm 14 in a bundle and go to sensor elements and/or electrical-signal receivers, such as the subcutaneous sensor shown at 18 in FIG. 1.

FIG. 2 shows a female connector 21, also supplied from the factory together with the socket 6, which is produced in the form of an annular cylindrical piece which is placed without any clearance in the space between the internal face of the shank 11 and the external face of a cylindrical stub 22 integral with the baseplate 16. In the system shown, the connector 21 comes into abutment with the support plate 17 which surrounds the stub 22. It is angularly positioned with respect to the support plate 17 by means of a lug 23, so that the ends of the electrical conductors of the arm 14 come into precise correspondence and into contact, each to each, with the electrical conductors 24 of the connector 21. The printed-circuit conductors are thus electrically connected individually to the pins of the female connector.

In its form as received from the factory, the socket 6 is closed by a plug 7 which is screwed onto an external thread on the shank 11 until it comes into abutment with the top of the socket at the ring 25. An O-ring seal 26 around the shank provides sealing at this point. The plug 7 does not necessarily come into contact with the upper end of the shank 11 and of the connector 24. On the contrary, provision may be made for this plug to be able to exist in various lengths, just like the transcutaneous stud 8 which will now be described.

As may be seen in FIG. 3, the stud 8 essentially consists of a cylindrical bush 31 which, by means of an internal thread 32, is screwed onto the shank 11 of the socket instead of the temporary plug 7. The seal 26 then fulfils the same sealing function as above at a moment when there is little bleeding during the second surgical installation step.

The bush 31 contains an extension piece 33, of cylindrical general shape, mounted in the factory so as to be slidably removable therefrom. In the position shown, this extension piece forms, in the lower part, a male connector 27 complementary to the female connector 21 of the socket.

During the second step for installing the implanted device, after screwing on the bush 31, the electrical pins 30 of the male connector of the extension piece 33 are automatically placed opposite the corresponding bores in the connector 21 until they come into electrical contact with the corresponding conductors 24, by means of a positioning pin 36, made of non-conducting material, which, having a slightly greater length than that of the conducting pins 30, enters a recess 37 cut out for this purpose in the connector 21.

It is during this operation that the positioning pin 36, like all the pins 30, perforates a sealing membrane 34 which is adhesively bonded at the outset to the upper end face of the connector 21.

This membrane has been shown in FIG. 2 in the case in which it covers only the connector 21. However, it will often be preferred for this membrane to extend beyond the latter until being adhesively bonded so as also to overlap the annular outermost face of the shank 11 of the socket, rather than resting only on the temporary plug for sealing the connector 21 in the socket. It may be seen, however, according to the figures, that in this case, since the membrane 34 has the essential role of protecting the conductors 24, it is advantageously perforated with a hole opposite the recess 37, in such a way that the position of this recess is visible in order to facilitate the suitable radial positioning of the male connector 27 when putting the stud 8, equipped with the extension piece 33, into place.

The two parts of the transcutaneous device are permanently fixed to each other by a screw 38 (FIG. 2) which, passing through an axial bore in the extension piece 33, also pierces the membrane 34 and is screwed into a threaded bore 39 in the baseplate 16.

The extension piece 33, which forms the male connector mating with the female connector 21 of the socket, in fact fulfils the role of an extension piece for electrical connections insofar as it also forms a female connector in its upper part 28, so as to connect thereat the external units 1 and 2 by any connection means having male pins, known per se. The latter are incorporated in a connection housing 41 (FIG. 2) which removably fits onto the bush 31 of the transcutaneous stud by virtue, in the particular case illustrated, of a bayonet-type system illustrated at 29 by tabs on the outside of the bush 31 of the stud.

A subcutaneous implant intended to complete the device according to the invention has been shown in FIG. 1 in the form of a conventional sensor 18 which is sensitive to the emission of electromagnetic energy on the surface of a muscle or other soft tissue in the body. The gold wire 19 is bonded thereto at its stripped end on the opposite side from the transcutaneous device 3 before putting the system into place.

FIGS. 4 and 5 show another type of sensor which will often be preferred to be used in combination with the implant 3, especially for an application consisting in monitoring epileptic diseases by encephalograms. These are then subcutaneous implants which are immobilized by fixing them to a bone, such as the bone of the cranium, at points suitably chosen by the physician.

Such a sensor implant 42 essentially consists of a screw 43 which has on the outside a thread of the type for an extra-oral implant, in this case an intra-osseous implant, and on the inside an axial threaded bore intended to receive a cover screw 44 through a nut 45 terminating the implant screw 43. The stripped end of the gold wire 29 is jammed in electrically conductive contact between the implant screw 43 and the cover screw 44. A recess intended to receive the wire in the internal threaded bore of the implant may be provided. The latter furthermore includes a washer having tabs inclined to the axis 46, helping to keep the implant in place in the bone by preventing it from unscrewing. A radial groove 47, on the surface of this washer, affords a passage for the wire 29. The latter leaves the subcutaneous implant 42 therefrom and goes to the transcutaneous device 3. A helical channel may also be provided on the external thread of the screw 43 in order to increase the bone/implant interfacial surface area.

Typical applications of the medical equipment device of the invention, once the transcutaneous device 3 has been put into place and electrically connected to the various subcutaneous sensors 18 or 42, advantageously use a method for medically examining the manifestations of the body's physiological activity, these possibly being pathological manifestations, the said method consisting in detecting the electromagnetic phenomena which they cause by means of sensors implanted directly inside the body and in transmitting them in the form of electrical signals to the outside.

The signal processing is in itself conventional, but the results are more detailed and more reliable than any which could have been obtained in the past, so that, for example, the apparatus in its entirety can be used to exploit nerve impulses or muscular exertions detected in situ in order to control a removable external prosthesis having electromechanical articulations.

In other words, a medical examination method involving the application of the equipment according to the invention is characterized in that sensors directly implanted in the body are used to detect electromagnetic phenomena induced by manifestations of physiological activity, in the form of electrical signals which are transmitted to the outside of the body through a permanent transcutaneous device which includes an implanted socket prevented from moving by being fixed to a bone and fastened to a stud which remains permanently accessible from the outside through the skin.

Of course, the invention is not limited by the particular features which have been specified in the foregoing or by the details of the particular embodiment chosen to illustrate the invention. In particular, a useful alternative form would consist in replacing the purely electrical conducting wires and pins described by electro-optical conductors, substituting the printed circuit with optical fibers embedded in the support plate 17 in an optoelectronic detection system.

In the alternative embodiment illustrated in FIG. 7, it may be seen that the base of the socket 6 and the baseplate 16 consist of a single piece. This therefore avoids adding the support plate 17 to it, the wires and conducting circuits being directly installed in the hollow space 51 made for this purpose in a special arm 52 of the socket 6, these terminating individually in the perforations in an annular support plate 53 to which these wires and conducting circuits are fixed.

The support plate 53 is mounted in the socket 6 within the volume of the shank 11 by means of a central screw. Its final position is predefined in terms of angular orientation in the shank 11, the latter having a groove 55 for centring the subsequent transcutaneous stud. Its axial position is limited, while it is being screwed on, by a circular stop on the socket which leaves under it a space 56 for passage of the conducting wires, having a radial access hole 57.

As in the alternative embodiment of FIG. 2, alternately the temporary plug 7 and the transcutaneous stud 61 are engaged on the shank 11 until they butt up against a ring 25 forming an additional thickness of the socket 6 around the shank 11. As this is the temporary plug, the electrical contacts at the end of the conducting wires in the support plate 53 are insulated by the sealing membrane 34.

It may therefore be seen that, according to one way of implementing the invention which will often be preferred in the case of industrial practice, mainly to reduce the manufacturing costs by simplifying the pieces and their mounting without thereby impairing the convenience and safety of use for surgeons and physicians, the functions of the female connector 21 of FIG. 1, with regard to the electrical connections to the circuits implanted in the body, are better provided by the electrical contacts accessible at the surface of the support plate 53. The latter therefore combines various functions which, in the above alternative form, would involve partly the female connector 21 and partly the support plate 17, while the mechanical construction of the socket and of its connection to the other components of the device is also simplified.

The embodiment illustrated in FIGS. 7 to 10 does not relate to this alternative form, but rather to particularly advantageous embodiments of the invention, separately or in their operating combinations, with regard mainly to the socket to be implanted in the body, the transcutaneous stud and the components providing the electrical connections, in a reliable manner, maintaining the paramount conditions of there being no biological contamination.

While FIG. 7 again shows the screw 38, with regard to the functions which have been described above, and also again shows the bayonet connection device 29 (except that the interacting shapes, some of them in the form of a protuberance and others in the form of a recess, are reversed), it may be observed that the bush 31 of the stud 8 has, on the inside, centering lugs, respectively 61 for engaging in a groove 62 of the extension piece 33 and 63 for engaging in the groove 55 of the shank 11 which has just been mentioned. These various features provide a predefined angular positioning of the various components involved in the electrical connections which are essential to the operation of the device of the invention.

Moreover, it will be observed that, inside the bush 31, there is, made as one piece with the bush, a spacer 65 constituting the connector for electrical connection. This spacer 65 has a central through-bore 66 which allows penetration of the screw 38 and which also allows the extension piece 33 to be placed in a predetermined position on an internal shoulder. Moreover, the spacer 65, in its annular region around the central bore 66, is drilled with holes 67 in which electrical connection pins 68 fitted beforehand into the extension piece 33 are positioned. By means of the engagement of centering lugs 61 and 63 in the interacting grooves 62 of the extension piece 33 and 55 of the shank 11 of the socket 6, the pins 68 are placed precisely through the holes 67, opposite the electrical contacts terminating the transmission wires within the support plate 53.

FIGS. 9 and 10 illustrate how a cap 71 for closing the transcutaneous device, fitted onto the stud 8, outside the body, may be replaced by a con-nector 72. Either one of them is screwed onto the bush 31 of the stud 8, on an external thread provided for this purpose, or is fixed thereto by means of a bayonet device. Passing through the connector 72 are wires 73 to be used for transmitting information or commands and/or for receiving data emitted in the body, to the external analysis devices. The connector 72 incorporates, as illustrated in FIG. 9, not only a seal 75 for connection to the bush 31, but also male pins 76 which are then plugged into the female pins 68 already described, so as to provide electrical connection to each.

I claim:

1. A medical equipment system for allowing electrical connections through the skin, comprising:
   a transcutaneous device having a socket comprising electrical connection means, means for fixing said socket to a bone in a body, and means for making a sealed connection thereto;
   a temporary plug for connection to said means for making a sealed connection;
   a transcutaneous stud for connection to said means for making a sealed connection when said temporary plug is not connected thereto, said stud comprising electrical connection pins complementary to said electrical connection means in said socket;
   said socket further comprising an impermeable membrane for bacteriological protection of said electrical connection means in said socket, said membrane being perforated by said electrically conducting pins when said stud is put into place as a replacement for said temporary plug.

2. The medical equipment system according to claim 1, wherein said electrical connection means comprises female connectors for mating with respective ones of said electrical connecting pins, and wherein said socket comprises a base having flanges at the end of which said means for fixing said socket to the bone are provided and an arm carrying electrical conductors to said female connectors.

3. The medical equipment system according to claim 2, wherein said arm is hollow.

4. The medical equipment system according to claim 2, wherein when said temporary plug is removed from said socket, said female connectors are protected by said membrane until said membrane is perforated.

5. The medical equipment system according to claim 2, wherein said female connectors comprise further pins in a spacer of a bush of said stud.

6. The medical equipment system according to claim 5, wherein said spacer has holes for electrical contact between said further pins and conducting wires in the body, through a support plate in said socket.

7. The medical equipment system according to claim 1, wherein said conductors are at least partly in the form of printed circuits embedded in a support plate contained in said arm.

8. The medical equipment system according to claim 1, wherein said electrical connection means comprises a female connector having a recess visible through said membrane for receiving a radial positioning pin extended from said stud.

9. The medical equipment system according to claim 1, wherein said stud comprises an extension piece and a bush for receiving said extension piece, said extension piece comprising connectors for receiving external electrical connectors.

10. The medical equipment system according to claim 1, further comprising one or more sensors subcutaneously implanted in the body.

11. The medical equipment system according to claim 10, wherein said sensor includes a screw for implanting in the bone, having an axial threaded bore for receiving a cover screw and conductive-contact jamming means for the end of a wire connected to said transcutaneous device.

12. The medical equipment system according to claim 11, wherein said sensor includes a washer for preventing unscrewing, which has a groove for passage of said wire.

13. The medical equipment system according to claim 10, wherein each said sensor is for being electrically connected to said socket through a wire running under the skin, and further comprising a removable external connector for transmission of electrical signals from said sensors.

14. A method of making electrical connections to a transcutaneous device having a socket, a temporary plug for covering the socket, a transcutaneous stud for connection to the socket when the temporary plug is not connected thereto, the stud having electrical connection pins complementary to female connectors in the socket, and an impermeable membrane for bacteriological protection of the female connectors in the socket, the method comprising the steps of:
   fixing, in a first surgical installation step, the socket to a bone in an animal or human body while it is covered with the temporary plug;
   removing, in a second surgical installation step, the temporary plug leaving the female connector protected by the membrane; and
   replacing the plug with the transcutaneous stud equipped with the pins which perforate the membrane and provide an electrical connection between the respective pins and the female connectors.

* * * * *

UNITED STATES PATENT AND TRADEMARK OFFICE
CERTIFICATE OF CORRECTION

PATENT NO. : 5,873,368
DATED : February 23, 1999
INVENTOR(S) : Pierre SABIN

It is certified that error appears in the above-identified patent and that said Letters Patent is hereby corrected as shown below:

On the title page, item [54], column 1, lines 1-3 change the title to.

--TRANSCUTANEOUS DEVICE AND METHOD FOR MAKING ELECTRICAL CONNEC-

TIONS THROUGH THE SKIN--.

Signed and Sealed this

Fifteenth Day of June, 1999

Attest:

Q. TODD DICKINSON

Attesting Officer

Acting Commissioner of Patents and Trademarks